United States Patent [19]

Fleischle

[11] Plant 4,962

[45] Dec. 7, 1982

[54] DISTINCT VARIETY OF STREPTOCARPUS NAMED AURORA

[75] Inventor: Gerhard Fleischle, Vaihingen, Fed. Rep. of Germany

[73] Assignee: Oglevee Associates, Inc., Connellsville, Pa.

[21] Appl. No.: 204,351

[22] Filed: Nov. 5, 1980

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Webb, Burden, Robinson & Webb

[57] ABSTRACT

A new variety of streptocarpus plant is characterized by its red flower having a yellow throat. It has large flowers and is generally nonfertile.

1 Drawing Figure

BACKGROUND OF THE NEW PLANT

The present invention comprises a new and distinct cultivar of Streptocarpus × *hybridus* known by the varietal name Aurora, formerly named Neptune Rot. The new cultivar is a mutation achieved through irradiation of Velma, formerly Neptune Rose (U.S. Plant Pat. No. 4,527). Aurora is virtually identical to Velma except for the color of the flower. The flower is most closely compared to Freda (U.S. Plant Pat. No. 4,528), but has more red and less purple than Freda. Aurora is more robust and prolific as compared to Freda and is similar to Velma in that regard.

The new cultivar was discovered in 1979 in Vaihingen, Federal Republic of Germany; was first asexually reproduced by cuttings in Vaihingen, Federal Republic of Germany and has been repeatedly asexually reproduced by cuttings at Oglevee Floral Company in Connellsville, Pa. It has been found to retain its distinctive characteristics through successive propagations.

DESCRIPTION OF THE DRAWING

The accompanying drawing illustrates the new cultivar.

DESCRIPTION OF THE NEW PLANT

The following detailed description sets forth the characteristics of the new cultivar. The data which defines these characteristics were collected from asexual reproductions carried out by Gerhard Fleischle at Vaihingen, Federal Republic of Germany. Color references are primarily to the R.H.S. color chart of the Royal Horticultural Society of London unless otherwise referenced. The color references were collected from asexual reproductions carried out by Oglevee Floral Company in Connellsville, Pa.

Botanical classification: Gesneriaceae (Family); Streptocarpus × *hybridus (Genus × Species).*

Flower:

*Fully expanded.*—Six centimeters.

*Borne.*—In clusters of one to six flowers per stalk above foliage. Flower stalks arise from mid-rib of each leaf.

*Stems.*—Single, long and pubescent.

*Form.*—Funnel formed in an umbel.

Color:

*Front of petal.*—Fan 2 Red Purple Group 74-A.

*Throat.*—Fan 1 Yellow Group 9-B with a plurality of stripes, Fan 2 Red Purple Group 67-B extending into center of petals.

*Base of petal.*—Fan 2 Red Purple Group 74-B.

*Reverse of petal.*—Fan 2 Red Purple Group 74-C.

*Tonality from a distance.*—Exotica 46 amethyst.

*Discoloration.*—Insignificant.

Petals:

*Texture.*—Velvet.

*Appearance.*—Individually lobed with ruffled to serrated margin.

*Arrangement.*—Regularly united into an elliptical form.

*Fragrance.*—None.

Reproductive organs:

*Anthers.*—Two per flower and interconnected.

*Filament.*—Two and one-half centimeters initiating from the base of the petal and extending to the anther.

*Pollen.*—Generally nonfertile.

*Style.*—Extends from the top of the ovary one centimeter and terminates in a flattened stigma.

*Ovaries.*—Long and narrow, one and one-half millimeters and one and one-half centimeters long.

Plant:

*Form.*—Leaves rosulete with a crown at the soil line.

*Growth.*—A spreading, free flowing habit with leaf bases being acute.

*Height from soil line.*—15 to 20 centimeters.

*Spread.*—35 to 40 centimeters.

Foliage:

*Size.*—Approximately 20 centimeters in length and 5 to 10 centimeters in width at the widest point.

*Quantity.*—10 to 15 leaves.

*Shape.*—Oblanceolate.

*Top side.*—Fan 3 Green Group 137-B.

*Underside.*—Fan 3 Yellow-Green Group 146-D.

*Rib and vein color.*—Fan 3 Green Group 138-D.

*Ribs and veins.*—Pinnate.

*Margin.*—Crenate serrations.

*Stipules.*—None.

I claim:

1. A new and distinct variety of streptocarpus substantially as herein shown and described.

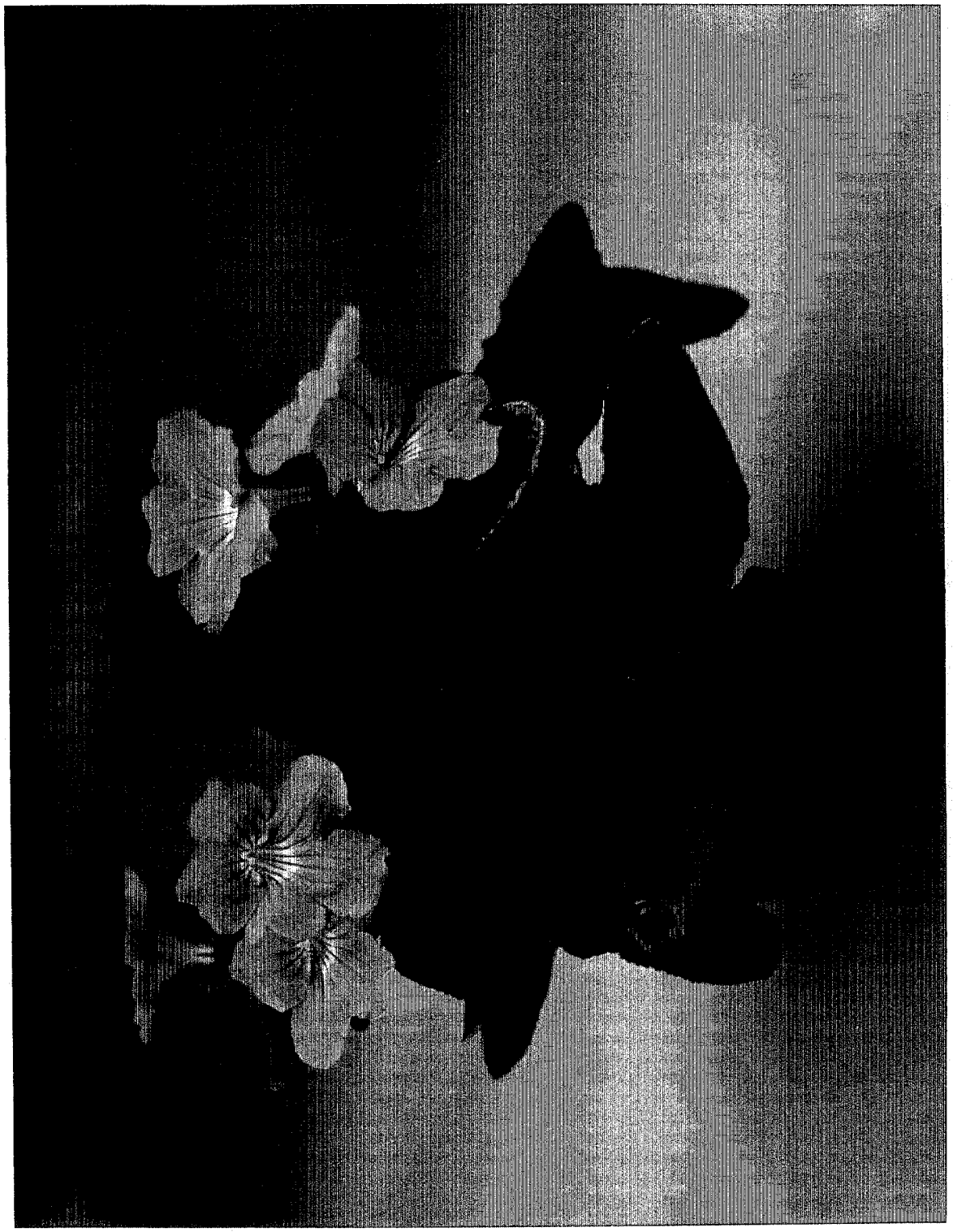

* * * * *